(12) United States Patent
Del Bono et al.

(10) Patent No.: US 12,005,075 B2
(45) Date of Patent: Jun. 11, 2024

(54) SUPPLEMENT FOR MITIGATING WOMAN'S DISORDERS CAUSED BY AGEING

(71) Applicant: CRISTALFARMA S.R.L., Milan (IT)

(72) Inventors: Maria Cristina Del Bono, Milan (IT); Francesco Bonomo, Milan (IT)

(73) Assignee: CRISTALFARMA S.R.L., Milano MI (IT)

( * ) Notice: Subject to any disclaimer, the term of this patent is extended or adjusted under 35 U.S.C. 154(b) by 0 days.

(21) Appl. No.: 17/659,185

(22) Filed: Apr. 14, 2022

(65) Prior Publication Data

US 2022/0233617 A1    Jul. 28, 2022

Related U.S. Application Data

(63) Continuation of application No. 16/754,851, filed as application No. PCT/IB2018/057886 on Oct. 11, 2018, now Pat. No. 11,433,109.

(30) Foreign Application Priority Data

Oct. 13, 2017  (IT) ................. 102017000115753

(51) Int. Cl.
| | | |
|---|---|---|
| A61K 33/30 | (2006.01) | |
| A23L 33/105 | (2016.01) | |
| A23L 33/15 | (2016.01) | |
| A23L 33/16 | (2016.01) | |
| A61K 9/00 | (2006.01) | |
| A61K 31/4415 | (2006.01) | |
| A61K 31/51 | (2006.01) | |
| A61K 31/525 | (2006.01) | |
| A61K 31/714 | (2006.01) | |
| A61K 33/06 | (2006.01) | |
| A61K 36/03 | (2006.01) | |
| A61K 36/185 | (2006.01) | |
| A61P 5/04 | (2006.01) | |
| A61P 17/00 | (2006.01) | |

(52) U.S. Cl.
CPC ............ *A61K 33/30* (2013.01); *A23L 33/105* (2016.08); *A23L 33/15* (2016.08); *A23L 33/16* (2016.08); *A61K 9/009* (2013.01); *A61K 31/4415* (2013.01); *A61K 31/51* (2013.01); *A61K 31/525* (2013.01); *A61K 31/714* (2013.01); *A61K 33/06* (2013.01); *A61K 36/03* (2013.01); *A61K 36/185* (2013.01); *A61P 5/04* (2018.01); *A61P 17/00* (2018.01)

(58) Field of Classification Search
CPC .................................. A16P 5/04; A16P 17/00
See application file for complete search history.

(56) References Cited

U.S. PATENT DOCUMENTS

| | | |
|---|---|---|
| 7,128,932 B2 | 10/2006 | Bombardelli et al. |
| 8,846,061 B1 | 9/2014 | Bezzek |
| 9,913,867 B2 | 3/2018 | Choi et al. |
| 10,967,025 B2 | 4/2021 | Vieira |
| 2007/0031486 A1 | 2/2007 | Squashic et al. |
| 2011/0159123 A1 | 6/2011 | Ditchfield |
| 2013/0017285 A1* | 1/2013 | Bhatia ............. A61K 8/44 424/769 |
| 2016/0038530 A1 | 2/2016 | Engholdt |
| 2016/0095879 A1 | 4/2016 | Bourgeois et al. |

FOREIGN PATENT DOCUMENTS

| | | |
|---|---|---|
| CN | 105707863 A | 6/2016 |
| CN | 106420500 A | 2/2017 |
| WO | 2006021930 A2 | 3/2006 |

OTHER PUBLICATIONS

Fatima et al., "Efficacy of *Tribulus terrestris* L. (fruits) in menopausal transition symptoms: A randomized placebo controlled study" Adv Int Med 4 (2017), 56-65. (Year: 2017).*
Search Report and Written Opinion of PCT/IB2018/057886 dated Mar. 4, 2019.
Zhang et al., "*Undaria pinnatifida* (Wakame): A seaweed with pharmacological properties", Science International, 2(2): 32-36, 2014 DOI: 10.17311/sciinti.2014.32.36.

* cited by examiner

*Primary Examiner* — Gina C Justice
(74) *Attorney, Agent, or Firm* — Silvia Salvadori, P.C.; Silvia Salvadori

(57) ABSTRACT

Combination of dry extract of *Rhodiola*, dry extract of *Trubulus terrestris*, dry extract of *Undaria pinnatifida, Moringa oleifera*, folic acid and vitamin B12 in the form of food supplement for mitigating woman's disorders caused by ageing.

9 Claims, 5 Drawing Sheets

Fig. 1

Zung Self-rating Depression Scale (SDS)

| Cross out the answer you deem most appropriate. | Occasionally | Sometimes | Frequently | Most of the time |
|---|---|---|---|---|
| 1. I feel sad and discouraged | | | | |
| 2. The morning is when I feel better | | | | |
| 3. I have nervous crises | | | | |
| 4. I have sleep problems | | | | |
| 5. I eat as I used to do | | | | |
| 6. I have a reduced sexual interest | | | | |
| 7. I notice that I am losing weight | | | | |
| 8. I have constipation problems | | | | |
| 9. My heart beats faster than usual | | | | |
| 10. I am tired without reason | | | | |
| 11. My mind is clear as it used to be | | | | |
| 12. I find it easy to make things as I used to do | | | | |
| 13. I am restless and cannot stand still | | | | |
| 14. I feel hopeful for the future | | | | |
| 15. I am more irritable than usual | | | | |
| 16. I find it simple to take decisions | | | | |
| 17. I feel useful and indispensable | | | | |
| 18. My life is sufficiently full | | | | |
| 19. I think others would be better off if I were not there? | | | | |
| 20. I still like things that I used to like | | | | |

Fig.2

FSFI questionnaire

SCALE 0-4 → 0(BEST CASE) - 4 (WORST CASE)

1. In the last 4 weeks, how often did you feel desire/sexual interest?

| Almost always or always | |
|---|---|
| Many times (more than half of the time) | |
| Sometimes (approximately half the time) | |
| A few times (less than half time) | |
| Almost never or never | |

2. In the last 4 weeks, how would you evaluate your desire/sexual interest?

| Very high | |
|---|---|
| High | |
| Middle | |
| Low | |
| Very low or absent | |

Sexual arousal is the feeling that includes both physical excitement and mental excitement. It may include a sensation of heat or stimulus at genital level, lubricating and/or vaginal muscle contraction.

3. In the last 4 weeks, how often did you feel energized during sexual activity and/or sexual intercourse?

| No sexual activity | |
|---|---|
| Almost always or always | |
| Many times (more than half of the time) | |
| Sometimes (approximately half the time) | |
| Sometimes (less than half time) | |
| Almost never or never | |

Physical appreciation questionnaire

| Questions | Scores | | | | |
|---|---|---|---|---|---|
| | 0<br>No improvement | 1<br>Slight improvement | 2<br>Moderate improvement | 3<br>Excellent improvement | 4<br>Great improvement |
| General physical appearance | | | | | |
| Hair health state | | | | | |
| Skin appearance improvement | | | | | |

SUPPLEMENT FOR MITIGATING WOMAN'S DISORDERS CAUSED BY AGEING

This application is a Continuation of U.S. Ser. No. 16/754,851, filed on Apr. 9, 2020, which is a U.S. national stage of PCT/IB2018/057886 filed 11 on October 2018, which claims priority to and the benefit of Italian Application No. 102017000115753 filed on 13 Oct. 2017, the contents of which are incorporated herein by reference in their entireties.

FIELD OF THE INVENTION

The present invention relates to a food supplement useful in promoting a better quality of life in women aged 45/50 years and older, mitigating the main characteristic disorders caused by ageing, such as sexual functioning changes, deterioration of connective tissue and skin appendages (skin, nails and hair) and mood disorders in addition to typical menopausal disorders.

STATE OF THE ART

The modalities of ageing are partly ascribable to genetic factors, even if environmental factors and lifestyle can alter this completely natural process. In women, the ageing process is associated with the alteration of the hormonal system, with affecting consequences on both general health and quality of life.

In fact, women aged 45/50 years and older are subject to sexual functioning disorders[1,2,3].

Sexual desire is the physical and mental need that motivates sexual activity in order to obtain gratification and to keep the couple's relationship steady. In the various stages of women's life, contextual factors are considerably relevant in modulating sexual health. The family of origin and the current family, as well as changes and losses, influence sexual experience at various levels.

From 45 to 50 years of age, vaginal dryness, dyspareunia and reduction of sexual pleasure are key factors that have a major influence on women's libido.

Testosterone is a hormone allied to women's health and not just with regard to sexual functioning. It activates the biological component of desire, mental and genital excitation, orgasm and physical satisfaction. Its maximum concentration in women is at the age of twenty and reduces dramatically with advancing age. Ageing and entry into menopause are associated with a progressive reduction of total testosterone concentrations, causing the loss of the essential biological component of desire.

This scenario is associated with the physiological ageing of tissues (the reduction of tissue trophism contributes to amplifying some imperfections to the detriment of those that are commonly considered symbols of femininity, such as skin, hair and nails.[1,2]

In fact, from the age of 45 years on, women are subject to skin alterations, such as thinning and reduction of the elastic component, which over time are manifested by dry skin and wrinkle appearance, hair loss and weakness and nail weakness.

Physiological changes are often accompanied by mental disorders, such as sudden changes in mood and depressive forms.[1,2] It is therefore felt the need to have a supplement that improves the general quality of life of women aged 45/50 years and older
    by acting on their sexuality, thus improving women libido,
    by slowing down the ageing of skin, mucous membranes and skin appendages (nails and hair),
    by restoring a general good mood.

Lately traditional medicine increasingly uses medical herbs, as they associate a good efficacy to a decidedly lower toxicity if compared to real drugs.

Even gynaecology does not escape this trend, so much so that these supplements increasingly represent a natural solution useful to counteract those disorders that, even if scarcely relevant, are very annoying and negatively affect the general well-being.

Food supplements generally used by women aged 45 years and older contain phytoestrogens or substances that bind to oestrogen cell receptors thus limiting their action. They are particularly effective in reducing hot flashes and are often associated with other substances such as magnesium and melatonin that promote sleep.

Other supplements are instead dedicated to supplementing calcium and vitamin D to counteract osteopenia, which can eventually lead to osteoporosis.

Therefore, all the supplements available on the market are mainly dedicated only to specific and most common menopausal disorders, but they are not dedicated to the restoration of a general well-being, thus neglecting the disorders of female ageing concerning sexuality, skin and skin appendages ageing and mood disorders.

The object of the present invention is to provide a food supplement that is able to mitigate the disorders which, from the middle age onwards, considerably affect the general quality of life of women, such as e.g. sexual disorders, skin and skin appendages ageing and mood disorders, thus contributing to the restoration of a general state of well-being of a woman going through this critical phase of life.

SUMMARY OF THE INVENTION

The applicant has now found that this is possible thanks to a combination comprising
    a) *Tribulus terrestris,*
    b) *Undaria pinnatifida,*
    c) *Moringa oleifera,*
    d) folic acid,
    e) vitamin B12,
    f) *Rhodiola.*

The object of the present invention is therefore the combination comprising the components a)-f) and its use in mitigating woman's disorders caused by ageing and therefore in ensuring her general well-being.

A further object of the present invention is a food supplement comprising the aforesaid combination together with suitable excipients and/or diluents as active ingredients.

DESCRIPTION OF THE FIGURES

FIG. 1 shows the questionnaire used to set the score for the self-rating depression scale (Zung Self-Rating Depression Scale (SDS)).

FIG. 2 shows the questionnaire used to set the score for the sexual disorders scale (Female Sexual Function Index FSFI).

Figure 6:
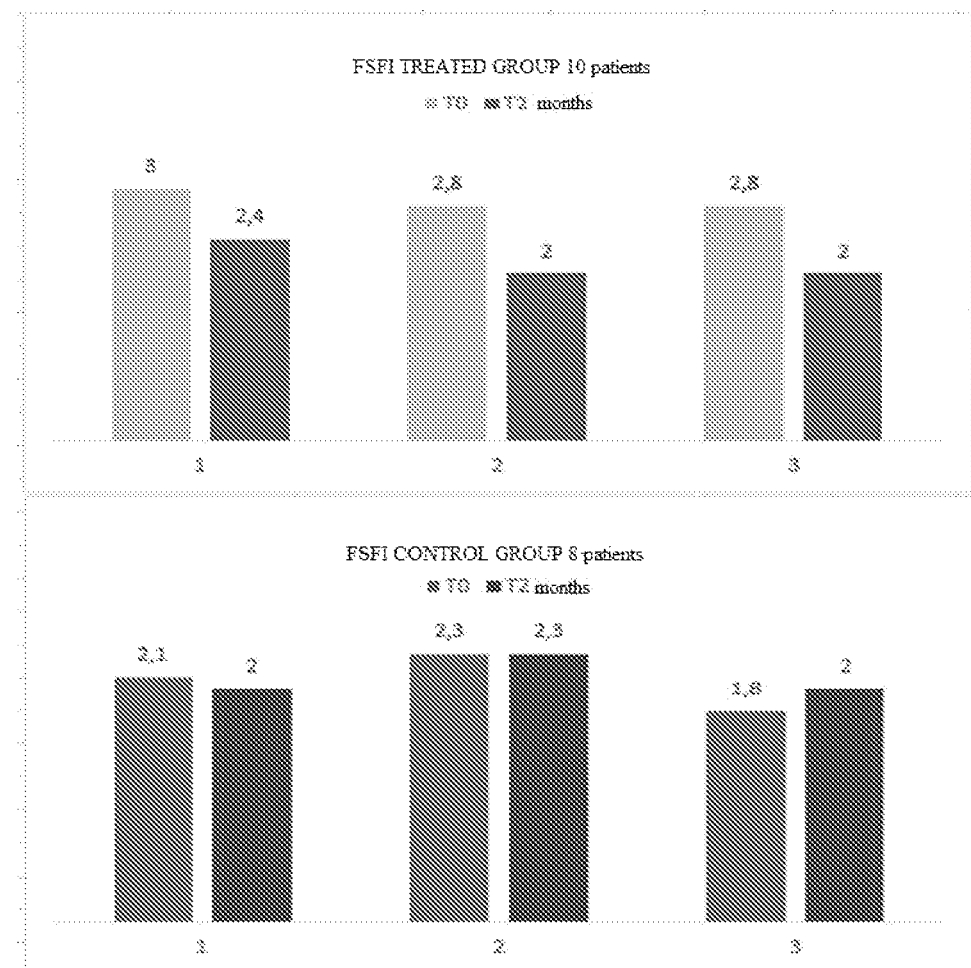

The upper panel of FIG. 6 shows in a graph the average values of the FSFI scores obtained with the treated patients, while the lower panel shows in a graph the same type of scores obtained with the control group.

Figure 7:
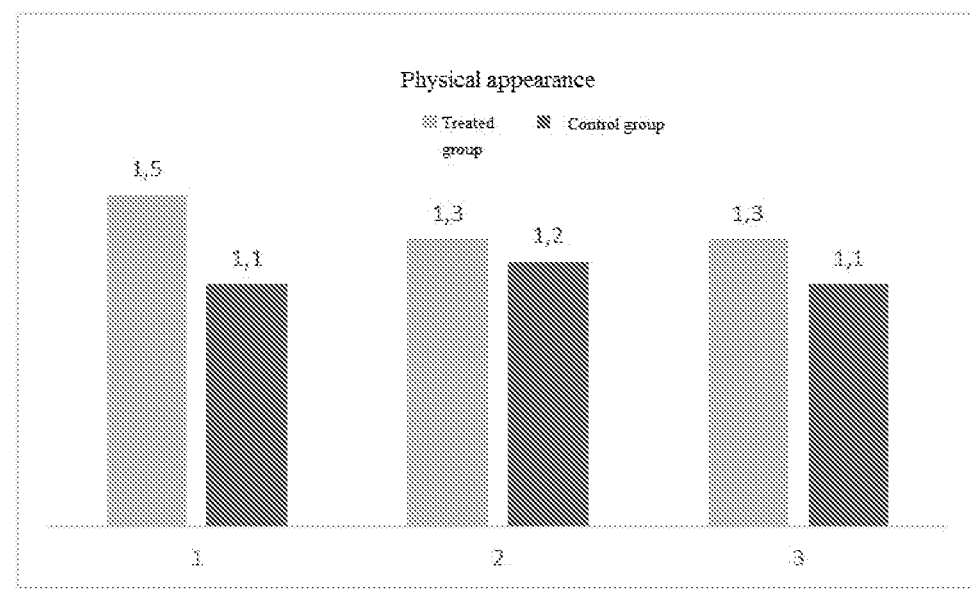

FIG. 7 shows in a graph the physical appreciation score of both treated patients and control group.

DETAILED DESCRIPTION OF THE INVENTION

For the purposes of the present invention, the expression "comprising/containing one or more components" does not exclude the presence of further components besides the one or more explicitly listed. For the purposes of the present invention, the expression indicating that an object "is made up or formed or composed of one or more components" means that the presence in the object of additional components besides the one or more listed components is excluded.

The combination comprising the components a)-f) is particularly suitable for alleviating sexual disorders, skin and skin appendages ageing and mood disorders.

The effectiveness of the combination object of the invention in mitigating sexual disorders is mainly attributable to *Tribulus terrestris*. Although recognized by the Ministry of Health as a tonic and metabolic support, in literature it is considered probably effective in counteracting female sexual dysfunction thanks to its activity, evaluated in preclinical studies on animals, which raises serum testosterone levels[4-7].

The Italian Ministry of Health associates with *Undaria pinnatifida* properties favouring nails and hair well-being, skin trophism and functionality, body weight balance and organism purifying functions. The literature associates these properties recognized by the tradition of use with antioxidant actions, body weight control by lowering fat mass regardless of diet and facilitation of energy metabolism. These actions are mainly attributed to the active ingredient fucoxanthin.[8-12]

*Moringa oleifera* is a plant of Indian origin with high nutritional values used for therapeutic purposes thanks to its phytochemical profile rich in biologically active molecules. Specifically, *Moringa oleifera* turned out to have antioxidant, anti-inflammatory and anti-hyperlipidaemic properties. It is also known for its blood circulation promoting action and as a body weight balancer.[13-19] In fact, the oestrogen deficiency due to menopause inevitably involves an increase of body weight caused by the blood increase of ("bad") LDL cholesterol, by the slowing of sugar metabolism as well as by the reduction of thyroid function.

Folic acid turned out to be effective in reducing the risk of mood alterations and brain damage in senile age[20], but also in reducing hot flashes in menopausal women[21].

Recent studies have shown that vitamin B12 deficiency may be an important modifiable risk factor for osteoporosis[22].

The combination object of the present invention is in particular effective for mitigating mood disorders mainly thanks to the presence of *Rhodiola*, which is a medical herb with adaptogenic action. Recent studies have shown that it stabilizes the mood of depressed subjects and is used to improve both physical and psychological performances associated with stressful conditions.[23-28] Preferably, the combination and consequently the food supplement can include one or more of the following active ingredients: magnesium, preferably in the form of oxide, and zinc, preferably in the form of pharmaceutically acceptable salts, thiamine (vitamin B1), riboflavin (vitamin B2) and vitamin B6.

Even more preferably, it consists of the components a)-f), magnesium, zinc, vitamin B1, vitamin B2 and vitamin B6.

With regard to magnesium, the regulation (EC) 432/2012 integrating the regulation (EC) 1924/2006 states that it contributes to:

maintaining normal bones;

reducing tiredness and fatigue;

normal muscle functioning;

normal psychological functioning;

maintaining normal bones and teeth.

With regard to zinc, the aforementioned regulation states that it contributes to:

normal cognitive functioning;

maintaining normal bones;

maintaining normal hair and nails.

With regard to thiamine, the aforementioned regulation states that it contributes to:

normal energy metabolism;

normal functioning of the nervous system;

normal psychological function;

normal cardiac function.

Finally, with regard to riboflavin, the aforementioned regulation states that it contributes to:

normal energy metabolism;

normal functioning of the nervous system;

maintaining normal membranes and mucous membranes;

maintaining normal red blood cells;

maintaining normal visual capacity;

normal iron metabolism;

protecting cells from oxidative stress;

reducing tiredness and fatigue.

For the purposes of the present invention, food or dietary supplements refer to the definition given in Article 2 of Legislative Decree No. 169 of 21 May 2004, i.e. they are foodstuffs intended to supplement the common diet and which constitute a concentrated source of nutrients, such as vitamins and minerals, or other substances having a nutritional or physiological effect, particularly, but not exclusively, amino acids, essential fatty acids, fibres and extracts of plant origin, both single- and multi-composites, in pre-dosed forms.

The food supplement further object of the present invention may be in the form of tablets, hard or soft capsules, powders or granules in the form of single-dose water dispersible sachets.

Preferably, it is in the form of sachets that can be administered only once a day.

*Rhodiola* included in the combination according to the present invention is preferably in the form of a dry root extract containing between 2 and 5% rosavine, namely a glycoside of cinnamic alcohol characterized by the following formula

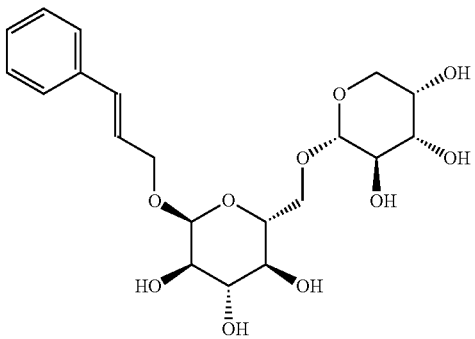 [SMILES: O[C@@H]1[C@@H](O)[C@@H](OC/C=C/c2ccccc2)O[C@H](CO[C@@H]2OC[C@H](O)[C@H](O)[C@H]2O)[C@H]1O]

The food supplement further object of the present invention in the most preferred form of a daily single-dose sachet contains Rhodiola in amounts preferably ranging from 175 to 225 mg, more preferably 200 mg.

In the combination according to the present invention, *Tribulus terrestris* is in the form of a dry extract preferably containing between 20 and 50% of saponins, which are terpenic glycosides.

In the food supplement in the preferred form of a daily single-dose sachet, *Tribulus* is contained in amounts preferably ranging from 150 to 200 mg, more preferably 175 mg.

In the combination object of the present invention the relative dry seed extract is used as the source of *Moringa*.

In the food supplement in the form of a daily single-dose sachet, this active agent is present in concentrations preferably ranging from 50 to 100 mg, more preferably 75 mg.

The combination object of the present invention uses a dry extract of *Undaria pinnatifida*, better known as Wakame algae, preferably containing between 8 and 12% of fucoxanthin, namely a xanthophyll of formula:

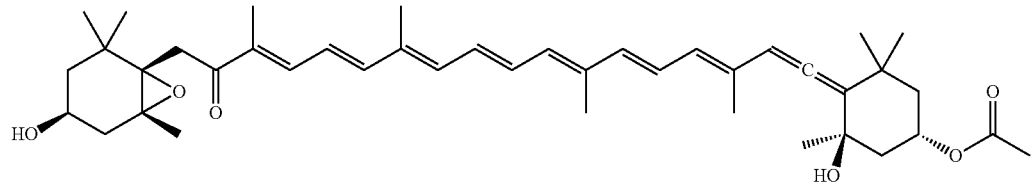 [SMILES: CC(=O)O[C@H]1CC(C)(C)C(=C=C/C(C)=C/C=C/C(C)=C/C=C/C=C(C)/C=C/C=C(\C)C(=O)C[C@@]23O[C@]2(C)C[C@@H](O)CC3(C)C)[C@](C)(O)C1]

*Undaria pinnatifida* is present in the supplement in the form of a single-dose sachet daily in concentrations preferably ranging from 20 to 30 mg, more preferably 25 mg.

Folic acid is instead present in the supplement in the form of single-dose sachets in amounts preferably ranging from 75 to 125 μg, more preferably 100 μg.

Vitamin B12 is preferably contained in the same type of supplement in amounts ranging from 1 to 1.6 μg, more preferably 1.5 μg.

When present in the food supplement according to the invention, magnesium is contained in an amount preferably ranging from 50 to 100 mg, more preferably 75 mg.

When present in the food supplement further object of the invention, zinc is preferably included in an amount ranging from 4 to 6 mg, more preferably 5 mg.

When present in the food supplement in the form of a daily single-dose sachet, vitamins B2 and B6 are preferably contained in amounts ranging from 0.6 to 0.8 mg, more preferably 0.7 mg.

When present in the food supplement in the form of a daily single-dose sachet according to the invention, vitamin B1 is preferably contained in amounts ranging from 0.45 mg to 0.60 mg, more preferably 0.55 mg.

The following table shows purely for illustrative but not limitative purposes in Example 1 below the following formulation in the form of a single-dose sachet.

Example 1

Food Supplement Formula (1 Sachet/Die from 4.5 gr)

| | DOSES FOR 1 sachet | VNR % |
|---|---|---|
| ACTIVE COMPONENTS | | |
| Rhodiola (*Rhodiola rosea* L., roots) rosavins titrated dry extract tot. | 200 mg | |
| Rosavins amount | 6 mg | |
| Tribulus (*Tribulus terrestris* L., fruit) saponins titrated dry extract per min., | 175 mg | |
| Saponins amount | 70 mg | |
| Moringa (*Moringa Oleifera* Lam., seeds) dry extract | 75 mg | |
| Magnesium | 75 mg | 20% |
| Wakame algae (*Undaria pinnatifida* (Harvey) Suringar, thallus) fucoxanthin titrated dry extract | 25 mg | |
| Fucoxanthin amount | 2.5 mg | |
| Zinc | 5 mg | 50% |
| Vitamin B6 | 0.7 mg | 50% |
| Riboflavin | 0.7 mg | 50% |
| Thiamine | 0.55 mg | 50% |
| Folic acid | 100 μg | 50% |
| Vitamin B12 | 1.25 μg | 50% |
| NON-ACTIVE COMPONENTS | | |
| Maltodextrins | 3,014 gr | |
| Citric acid - E330 | 250 mg | |
| Silicon dioxide - E551 | 150 mg | |

-continued

| | DOSES FOR 1 sachet | VNR % |
|---|---|---|
| Aromas | 110 mg | |
| Polyoxyethylene sorbitan monooleate - E433 | 50 mg | |
| Sucralose - E955 | 15 mg | |

Clinical Study

Rational

The way everyone ages is partly due to genetic factors. Ageing also combines environmental factors and lifestyle and leads to the slowing down of key processes and natural biological functions. In women, the ageing process is associated with the alteration of the hormonal structure with an impact on both general health and quality of life. Women aged 40 years and older often show:

Sexual Disorders[1,2,3]

Sexual desire is the physical and mental need that motivates sexual activity to achieve gratification. In the various stages of women's life, contextual factors are of considerable importance in modulating sexual health. The family of origin and the current family, as well as changes and loss events, influence sexual experience at various levels.

In women aged 40 years and older (peri-menopause) vaginal dryness, dyspareunia, reduction of sexual pleasure are key factors that have a major influence on women's libido.

Testosterone is a hormone allied to women's health and not just with regard to sexual functioning. It activates the biological component of desire, mental and genital excitation, orgasm and physical satisfaction. Its maximum concentration in women is at the age of twenty and reduces dramatically with advancing age. Menopause deprives women of high percentages of total testosterone, thus causing a loss of the essential biological component of desire.

Emotional Disorders[1,2]

Physiological changes are often accompanied by mental disorders such as sudden changes in mood, anxiety and depressive forms.

Deterioration of Connective Tissue and of Skin Appendages[1,2]

Skin alterations, such as thinning and reduction of the elastic component, which over time are manifested by dry skin and wrinkle appearance.

Hair loss and weakness.

Nail weakness.

Scope

From a clinical point of view, the general quality of life of women aged 40 years and older could be improved by slowing and mitigating the ageing disorders mainly by intervening on:
1. Sexual factors→couple well-being
2. Psychological factors→mood
3. Aesthetic factors→skin, mucous membranes, skin appendages (nails and hair)

Purpose
1. Promoting an improvement of libido
2. Restoring a General Good Mood
3. Improving the Overall Patient QOL
4. Aesthetic Factors→Better Stress Physical Perception Aim The aim of the present study is to evaluate whether the food supplement object of the present invention administered on patients with altered mood and reduced sexual function index can improve the quality of life of the women under observation.

Primary End Point

QOL improvement of migraine subjects through the analysis of the PGWBI questionnaire, given at baseline (T0) and 8 weeks after baseline (T2). The questionnaire will be given by the investigating doctor during the 2 protocolled visits corresponding to the two aforesaid trial times.

Secondary End Points

Mood evaluation through the Zung Self-Rating Depression Scale (SDS) questionnaire, given at baseline (T0) and 8 weeks after baseline (T2). The questionnaire is then given by the investigating doctor during the 2 protocolled visits corresponding to the two aforesaid trial times.

Evaluation of the FSFI sexual function index (self-built test), given at baseline (T0) and 8 weeks after baseline (T2). The questionnaire is then given by the investigating doctor during the 2 protocolled visits corresponding to the two aforesaid trial times.

Evaluation of one's own physical appreciation through a self-built questionnaire given after 8 weeks of observation (T2)

Dosage (1 Sachet/Day with Active Ingredients Present in the Same Amounts Shown in Table 1)

Criteria of Patient Enrollment

Twenty patients were enrolled according to the following inclusion and exclusion criteria.

Inclusion Criteria

They were consecutively enrolled: patients aged >40 years and with a reduced general quality of life due to mood disorders and sexual functioning alterations, who signed the INFORMED CONSENT FORM, only patients with a total response score appropriately recoded were included in the study, >60 to the PGWBI questionnaire reported below.

1. In the last 4 weeks how did you generally feel? (Select an answer)

| | |
|---|---|
| In an excellent mood | 5 |
| In a good mood | 4 |
| In a good mood for most of the time | 3 |
| With many ups and downs | 2 |
| Feeling down for most of the time | 1 |
| Depressed | 0 |

2. In the last 4 weeks did you suffer from illness, physical disorders or pain? (Select an answer)

| | |
|---|---|
| All days | 0 |
| Almost all days | 1 |
| For about half the time | 2 |
| Several times, but for less than half the time | 3 |
| Rarely | 4 |
| Never | 5 |

3. In the last 4 weeks did you feel depressed? (Select an answer)

| | |
|---|---|
| Yes, to the point of thinking of putting an end to it | 0 |
| Yes, to the point that I did not care about anything anymore | 1 |
| Yes, I felt very depressed almost all days | 2 |
| Yes, I felt rather depressed several times | 3 |
| Yes, I felt a little depressed sometimes | 4 |
| No, I never felt depressed | 5 |

4. In the last 4 weeks, did you feel in control of situations, thoughts, emotions and feelings? (Select an answer)

| | |
|---|---|
| Yes, definitely | 5 |
| Yes, almost entirely | 4 |
| Yes, generally | 3 |
| Not too much | 2 |
| No, and this disturbs me a little | 1 |
| No, and this disturbs me very much | 0 |

5. In the last 4 weeks did you feel annoyed by stress or because your nerves were on edge? (Select an answer)

| | |
|---|---|
| Greatly, enough not to be able to work or take care of things that I had to do | 0 |
| Quite a lot | 1 |
| Very much | 2 |

| | |
|---|---|
| Enough to be annoyed | 3 |
| A little | 4 |
| Not at all | 5 |

6. In the last 4 weeks, how much energy or vitality you had or you felt to have? (Select an answer)

| | |
|---|---|
| Definitely full of energy - very lively | 5 |
| Quite full of energy most of the time | 4 |
| I had considerable highs and lows of vitality and energy | 3 |
| My level of energy or vitality was generally low | 2 |
| My level of energy or vitality was almost always very low | 1 |
| I was powerless, emptied, devoid of energy or vitality | 0 |

7. In the last 4 weeks, did you feel discouraged or sad? (Select an answer)

| | |
|---|---|
| Never | 5 |
| Almost never | 4 |
| A part of the time | 3 |
| A lot of time | 2 |
| Almost always | 1 |
| Always | 0 |

8. In the last 4 weeks were you stressed or under pressure? (Select an answer)

| | |
|---|---|
| Yes, I was extremely stressed for all or nearly all the time | 0 |
| Yes, I was very stressed for most of the time | 1 |
| Generally no, but I felt quite stressed several times | 2 |
| Sometimes I felt a bit stressed | 3 |
| My pressure level was quite low | 4 |
| I never had the feeling of being stressed | 5 |

9. In the last 4 weeks, how much did you feel happy and satisfied or pleased of your life? (Select an answer)

| | |
|---|---|
| Really very happy - I could not feel more satisfied or happy | 5 |
| Almost always very happy | 4 |
| In general very satisfied - happy | 3 |
| Sometimes quite happy, sometimes rather unhappy | 2 |
| In general dissatisfied or unhappy | 1 |
| Almost always or always very dissatisfied or unhappy | 0 |

10. In the last 4 weeks, did you feel so well that you could do what you wanted or needed to do? (Select an answer)

| | |
|---|---|
| Yes, definitely | 5 |
| Yes, to do almost everything that I wanted or I needed to do | 4 |
| My health problems limited me in some important things | 3 |
| Because of my health I was barely able to take care of myself | 2 |
| I needed some help to take care of myself | 1 |
| I needed help for everything or almost everything I needed to do | 0 |

11. In the last 4 weeks, did you feel so sad, discouraged, desperate or had so many problems that you wondered whether it was worth going on? (Select an answer)

| | |
|---|---|
| Yes, greatly, enough to be almost on the point of letting it all go | 0 |
| Yes, quite a lot | 1 |
| Yes, very much | 2 |
| Yes, enough to disturb me | 3 |
| A little | 4 |
| Not at all | 5 |

12. In the last 4 weeks, did you wake up fresh and rested? (Select an answer)

| | |
|---|---|
| Never | 0 |
| Almost never | 1 |
| A part of the time | 2 |
| A lot of time | 3 |
| Almost always | 4 |
| Always | 5 |

13. In the last 4 weeks, did you feel apprehension, concern or fear for your health? (Select an answer)

| | |
|---|---|
| Enormously | 0 |
| Quite a lot | 1 |
| Very much | 2 |
| A bit, but not so much | 3 |
| Almost never | 4 |
| Not at all | 5 |

14. In the last 4 weeks, did you ever had reasons to ask yourself whether you were losing your mind or you were losing control of your memory because of how you acted, spoke, thought or heard? (Select an answer)

| | |
|---|---|
| Not at all | 5 |
| Only a little | 4 |
| A few reasons, but not enough to cause me apprehension or concern | 3 |
| A few reasons, enough to cause me a bit of concern | 2 |
| A few reasons, enough to cause me some concern | 1 |
| Yes, many reasons and I am quite worried | 0 |

15. In the last 4 weeks, your daily life was interesting to you? (Select an answer)

| | |
|---|---|
| Never | 0 |
| Almost never | 1 |
| A part of the time | 2 |
| A lot of time | 3 |
| Almost always | 4 |
| Always | 5 |

16. In the last 4 weeks, did you feel active, strong or slow, sluggish? (Select an answer)

| | |
|---|---|
| Always very active and strong | 5 |
| Almost always active and strong - never really slow and sluggish | 4 |
| Quite active and strong - rarely slow and sluggish | 3 |
| Quite slow and sluggish - rarely active and strong | 2 |
| Almost always slow and sluggish - never really active and strong | 1 |
| Always very slow and sluggish | 0 |

17. In the last 4 weeks, did you feel apprehension, concern or fear for your health? (Select an answer)

| | |
|---|---|
| Enormously, enough to feel unwell or nearly unwell | 0 |
| Quite a lot | 1 |
| Very much | 2 |
| Enough to disturb me | 3 |

| | |
|---|---|
| A little | 4 |
| Not at all | 5 |

18. In the last 4 weeks, did you feel emotionally stable and sure of yourself? (Select an answer)

| | |
|---|---|
| Never | 0 |
| Almost never | 1 |
| A part of the time | 2 |
| A lot of time | 3 |
| Almost always | 4 |
| Always | 5 |

19. In the last 4 weeks, did you feel relaxed, calm or very tense, nervous or agitated? (Select an answer)

| | |
|---|---|
| Always relaxed and calm | 5 |
| Almost always relaxed and calm | 4 |
| Generally calm and relaxed, but sometimes quite tense | 3 |
| Generally very tense, but sometimes fairly relaxed | 2 |
| Almost always very tense, nervous or agitated | 1 |
| Always very tense, nervous, or agitated | 0 |

20. In the last 4 weeks, did you feel happy and serene? (Select an answer)

| | |
|---|---|
| Never | 0 |
| Almost never | 1 |
| A part of the time | 2 |
| A lot of time | 3 |
| Almost always | 4 |
| Always | 5 |

21. In the last 4 weeks, did you feel tired, exhausted, frayed or worn out? (Select an answer)

| | |
|---|---|
| Never | 5 |
| Almost never | 4 |
| A part of the time | 3 |
| A lot of time | 2 |
| Almost always | 1 |
| Always | 0 |

22. In the last 4 weeks, were you or did you feel under pressure? (Select an answer)

| | |
|---|---|
| Yes, almost more than I could withstand or hold | 0 |
| Yes, very much | 1 |
| Yes, quite more than usual | 2 |
| Yes, enough, but almost as usual | 3 |
| Yes, a little | 4 |
| Not at all | 5 |

Exclusion Criteria

They were excluded from the trial: patients aged <40 years with obvious disorders on QOL, mood and even a mild sexual function impairment; patients with diagnosed neuro-psychiatric diseases; patients in early menopause; patients on hormone therapy or patients who had finished hormone therapy; patients in surgical and/or pharmacologically induced menopause; pregnant and/or lactating patients; patients familiar with oestrogen-dependent oncological diseases.

Study Design

This is an open pilot study.

10 of the 20 patients took once a day for 2 months a single-dose water dispersible sachet whose active composition is shown in Table 1.

The other 10 patients, namely the control group, did not take any medicament (neither phyto nor drug) and were all the same under observation for 2 months.

The efficacy of the formulation for use according to the present invention was evaluated through the score obtained with the patients' answers to the following questionnaires:
  the aforesaid PGWBI Questionnaire. The overall QOL improves if the values at the end of the clinical study increase.
  the self-rating depression scale questionnaire (Zung Self-Rating Depression Scale (SDS)), which was designed by W. W. Zung to check the level of depression for patients who have been diagnosed with a depressive disorder. Zung SDS is a monitoring measured by the patient to verify his/her level of depression. The scale has 20 questions, which allow evaluating the level of the four common characteristics of depression: pervasive effect, physiological equivalents, other disorders and psychomotor activities. This questionnaire shown in FIG. 1 consists of 10 questions asked in the negative and of 10 questions asked in the affirmative. The answer to each question is counted on a score scale from 1 to 4, which indicate respectively: for a short time, for a certain period of time, frequently, for most of the time. The total scores may vary from 25 to 100, and are so classified: 25-49 score interval of a non-depressed patient; 50-59 score interval of a slightly depressed patient, 60-69 score interval of a moderately depressed patient, >70 score of a severely depressed patient. There is always an improvement of the Zung SDS scale when the scores decrease.
  the FSFI sexual function questionnaire shown in FIG. 2. This is a self-built test. These questions are related to the patient's sexual life in the last 4 weeks. Desire and/or sexual interest means the desire to have a sexual experience, the feeling of being willing to respond to the partner's sexual initiative and/or thinking/fantasizing about having sexual intercourse. Sexual function improves when the average of the test scores is reduced.
  the self-built questionnaire shown in FIG. 3 about one's physical appreciation.

The trial timing is as follows:
T0: the PGWBI questionnaire is given to verify whether the patient can be enrolled. If she is suitable, the SDS, FSFI and PHYSICAL APPRECIATION questionnaires are given and the product for the first 4 weeks of treatment is delivered.
T2: second check-up, compilation of questionnaires, report drafting and filled database submission Results

PGWBI

Figures 3, 4:
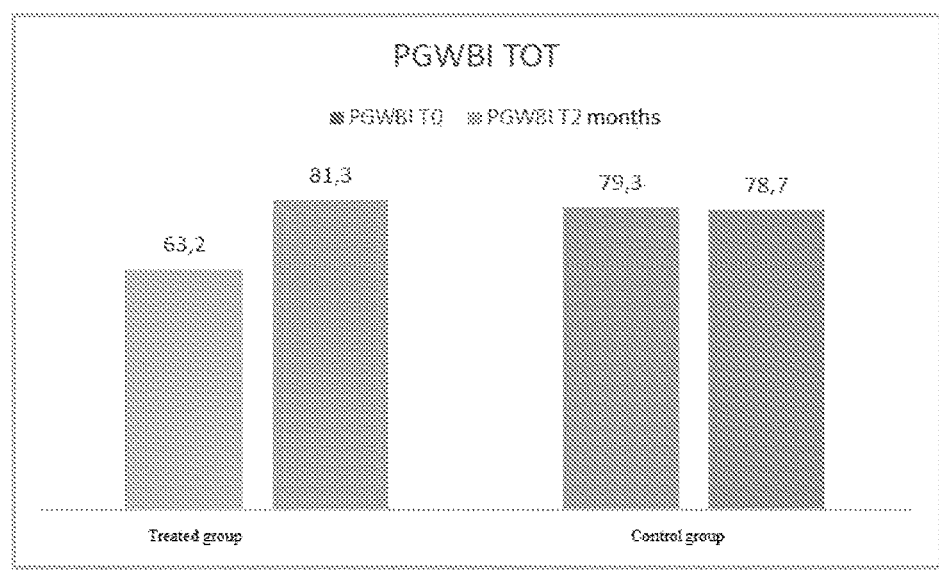
FIG. 3 shows the questionnaire used to set the score for the physical appreciation scale.
FIG. 4 shows in a graph the average total Psychological General Well-Being Index (PGWBI) of the treated patients and of the control group.
Figure 5:
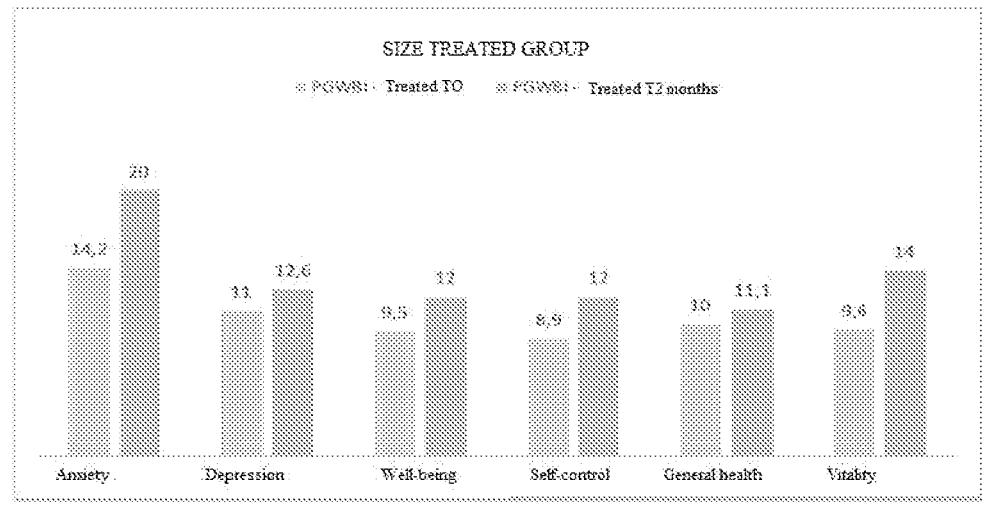
FIGS. 5 and 5A show in a graph the average values of the single aspects of PGWBI, respectively of the treated patients and of the control group.
Figure 5A:
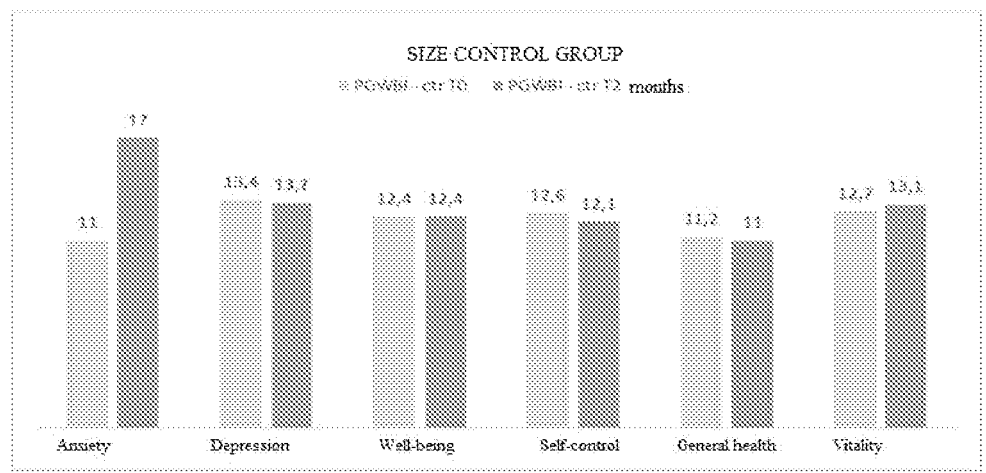

The results are shown in the graph shown in FIG. 4. The formulation object of the invention improves the women's QOL by increasing the test score by +30%. In particular, as shown by the graphs of FIGS. 5 and 5A, the formulations according to the present invention favour the QOL by intervening mainly on the items:

Apathy/depr (0-25)
Sense of well-being (1-15)
Self-monitoring (0-20)
General health status (0-15)
Sense of vitality (0-20)
ZUNG SDS As shown by the graph in FIG. 6, the people from treated group improve their mood, while the control group tends to get worse.

FSFI—Sexual Functioning
As shown by the graph in FIG. 6, the treated group:
Improves the frequency of sexual desire
Improves the judgment on one's sexual desire
Improves excitement.

On the contrary, no significant variations are observed in the control group, as shown in FIG. 6A.

Physical Appreciation
Patients noticed a slightly more marked improvement than the control group, as shown in FIG. 7.

BIBLIOGRAPHY

1. Graziottin A et al. Uso del testosterone nella donna. Aggiornamento medico; 32 (6). 2008
2. Orthman N, Nappi R. Benessere in menopausa. Ii vademecum di O.N.Da. osservatorio nazionale sulla salute della donna O.N.Da. 2014
3. Baldi S. et al. Disfunzioni sessuali femminili in peri-postmenopausa. Linee Guida Menopausa AOGOI (EDITEAM). 2007, 78-87
4. Sóstenes Postigo et al. Assessment of the Effects of *Tribulus Terrestris* on Sexual Function of Menopausal Women. Rev Bras Ginecol Obstet. 38, 140:146. 2016
5. Carlos R. B. Gama et al. Clinical Assessment of *Tribulus terrestris* Extract in the Treatment of Female Sexual Dysfunction. Clinical Medicine Insights: Women's Health 2014
6. Jameel M. et al. Pharmacological scientific evidence for the promise of *Tribulus terrestris*. IRJP. 2012
7. 7Walid H. El-Tantawy et al. Free Serum Testosterone Level in Male Rats Treated with *Tribulus alatus* Extracts. International Braz J Urol. 33 (4); 554:559. 2007
8. D'Orazio N A et al. Fucoxanthin: A Treasure from the Sea. Mar. Drugs. 10, 604-616. 2012
9. Meng-Ting Wu et al. Dietary Fucoxanthin Increases Metabolic Rate and Upregulated mRNA Expressions of the PGC-1alpha Network, Mitochondrial Biogenesis and Fusion Genes in White Adipose Tissues of Mice. Mar. Drugs. 12, 964-982. 2014
10. Sidney J. Stohs et al. A Review of Natural Stimulant and Non-stimulant Thermogenic Agents. Phytother. Res. 30: 732-740. 2016
11. Ae Wha Ha et al. The effect of fucoxanthin rich power on the lipid metabolism in rats with a high fat diet. Nutrition Research and Practice. 7(4):287-293. 2013
12. Jian Zheng et al. Fucoxanthin Enhances the Level of Reduced Glutathione via the Nrf2-Mediated Pathway in Human Keratinocytes. Mar. Drugs. 12, 4214-4230. 2014
13. Ganatra Tej as H et al. A panoramic view on pharmacognostic, pharmacological, nutritional, therapeutic and prophylactic values of *Moringa oleifera* Lam. International research journal of pharmacy; 3 (6). 2012
14. Muhammad N. et al. Promising features of *Moringa oleifera* oil: recent updates and perspectives. Lipids in Health and Disease; 15-212; 2016
15. Sathaporn N. et al. *Moringa Oleifera* Leaf Extract Increases Plasma Antioxidant Status Associated with Reduced Plasma Malondialdehyde Concentration without Hypoglycemia in Fasting Healthy Volunteers. Chin J Integr Med. 2016
16. Majambu M. et al. Therapeutic potential of *Moringa oleifera* leaves in chronic hyperglycemia and dyslipidemia: a review. Frontiers in pharmacology. 24 (3). 2012
17. Masoumeh Tangestani Fard et al. Bioactive Extract from *Moringa oleifera* Inhibits the Pro inflammatory Mediators in Lipopolysaccharide Stimulated Macrophages. Pharmacogn Mag. 11(4). 2015
18. Elizabeth I. et al. Hepatoprotective, Antihyperlipidemic, and Anti-inflammatory Activity of *Moringa oleifera* in Diabetic-induced Damage in Male Wistar Rats. Pharmacognosy Res. 9(2): 182-187. 2017
19. Lakshmipriya G. et al. *Moringa oleifera*: A review on nutritive importance and its medicinal application. Food Science and Human Wellness. 5, 49-56. 2016
20. E H Reynolds. Folic acid, ageing, depression, and dementia. BMJ, 324. 2002
21. S. Bani et al "The effect of folic acid on Menopausal Hot Flashes. A randomized clinical trial" doi 10.5681/jcs 2013.016, Journal of Caring Science, June 2013, 2(2) 131-140.
22. Katherine L Tucker et al. Low Plasma Vitamin B12 Is Associated With Lower BMD: The Framingham Osteoporosis Study. journal of bone and mineral research. 20 (1). 2005.
23. Alexander P et al. The Adaptogens *Rhodiola* and *Schizandra* Modify the Response to Immobilization Stress in Rabbits by Suppressing the Increase of Phosphorylated Stress-activated Protein Kinase, Nitric Oxide and Cortisol. Drug Target Insights. 2, 39:54 2007
24. Jay D. Amsterdam et al. *Rhodiola rosea* L. as a putative botanical antidepressant. Phytomedicine. 23; 770:783. 2016
25. Jun J Mao et al. *Rhodiola rosea* therapy for major depressive disorder: a study protocol for a randomized, double-blind, placebo-controlled trial. J Clin Trials. 2015.
26. Assessment report on *Rhodiola rosea* L., rhizoma et radix. EMA. 2011.
27. Eric Noreen et al. The effects of an acute dose of *Rhodiola rosea* on exercise performance and cognitive function. Journal of the International Society of Sports Nutrition 2009
28. A. A. Spasov et al. A double-blind, placebo-controlled pilot study of the stimulating and adaptogenic effect of *Rhodiola rosea* SHR-5 extract on the fatigue of students caused by stress during an examination period with a repeated low-dose regimen. Phytomedicine. 7(2), 85:89. 2000.

The invention claimed is:
1. A method of treating woman's disorders caused by ageing, wherein said woman's disorders are sexual disorders, deterioration of connective tissue and skin appendages, mood disorders and menopausal disorders, said method comprising
administering a food supplement comprising:
a) *Tribulus terrestris,*
b) *Undaria pinnatifida,*
c) *Moringa oleifera,* d) Folic acid,
e) Vitamin B12,
f) *Rhodiola*,
and suitable excipients and/or diluents,
wherein the food supplement is administered once a day.

2. The method according to claim 1, wherein the food supplement further comprises at least one of the following active ingredients:
g) Magnesium,
h) Zinc,
i) Vitamin B1,
j) Vitamin B2, or
k) Vitamin B6.

3. The method according to claim 1, wherein said woman's disorders are flushing, osteopenia, vaginal dryness, decline in sexual desire and skin and cutaneous appendages ageing.

4. The method according to claim 1, wherein said sexual disorder is dyspareunia.

5. The method according to claim 1, wherein the food supplement is in form of tablets, rigid capsules, soft capsules, powders, or granulates in form of water dispersible single-dose sachets.

6. The method according to claim 5, wherein the food supplement is administered daily in the form of a water dispersible single-dose sachet, the food supplement comprising:
*Rhodiola* in amounts ranging from 175 to 225 mg;
*Tribulus terrestris* in amounts ranging from 150 to 200 mg;
*Moringa oleifera* in amounts ranging from 50 to 100 mg;
*Undaria pinnatifida* in amounts ranging from 20 to 30 mg;
Folic acid in amounts ranging from 75 to 125 μg;
Vitamin B12 in amounts ranging from 1 to 1.6 μg;
Magnesium in amounts ranging from 50 to 100 mg;
Zinc in amounts ranging from 4 to 6 mg;
Vitamins B2 and B6, each in amounts ranging from 0.6 to 0.8 mg;
Vitamin B1 in amounts ranging from 0.45 mg to 0.60 mg and
suitable excipients and/or diluents.

7. The method according to claim 5, wherein the food supplement consists of
*Rhodiola* in an amount of 200 mg;
*Tribulus terrestris* in an amount of 175 mg;
*Moringa oleifera* in an amount of 75 mg;
*Undaria pinnatifida* in an amount of 25 mg;
Folic acid in an amount of 100 μg;
Vitamin B12 in an amount of 1.5 μg;
Magnesium in an amount of 75 mg;
Zinc in an amount of 5 mg;
Vitamins B2 and B6, each in amount of 0.7 mg;
Vitamin B1 in an amount of 0.55 mg,
and suitable excipients and/or diluents.

8. A method of treating woman's disorders caused by ageing, wherein said woman's disorders are sexual disorders, deterioration of connective tissue and skin appendages, mood disorders and menopausal disorders, said method comprising administering a food supplement comprising:
*Tribulus terrestris*,
*Undaria pinnatifida*,
*Moringa oleifera*,
Folic acid,
Vitamin B12,
*Rhodiola*,
Magnesium,
Zinc,
Vitamin B1,
Vitamin B2, and
Vitamin B6,
and suitable excipients and/or diluents,
wherein the food supplement is administered once a day, and wherein
Vitamin B12 in amounts ranging from 1 to 1.6 vg;
Vitamins B2 and B6, each in amounts ranging from 0.6 to 0.8 mg;
Vitamin B1 in amounts ranging from 0.45 mg to 0.60 mg;
Folic acid in amounts ranging from 75 to 125 vg.

9. The method according to claim 8, wherein the food supplement is administered in the form of a water dispersible single-dose sachet, the food supplement comprising:
*Rhodiola* in amounts ranging from 175 to 225 mg;
*Tribulus terrestris* in amounts ranging from 150 to 200 mg;
*Moringa oleifera* in amounts ranging from 50 to 100 mg;
*Undaria pinnatifida* in amounts ranging from 20 to 30 mg;
Folic acid in amounts ranging from 75 to 125 vg;
Vitamin B12 in amounts ranging from 1 to 1.6 vg;
Magnesium in amounts ranging from 50 to 100 mg;
Zinc in amounts ranging from 4 to 6 mg;
Vitamins B2 and B6, each in amounts ranging from 0.6 to 0.8 mg;
Vitamin B1 in amounts ranging from 0.45 mg to 0.60 mg and suitable excipients and/or diluents.

* * * * *